United States Patent
Paterson et al.

(10) Patent No.: US 10,723,763 B2
(45) Date of Patent: Jul. 28, 2020

(54) USE OF TIGHT JUNCTION ANTAGONISTS IN THE TREATMENT OF ACUTE LUNG INJURY AND ACUTE RESPIRATORY DISTRESS SYNDROME

(71) Applicants: University of Maryland, Baltimore, MD (US); Alba Therapeutics Corporation, Baltimore, MD (US)

(72) Inventors: Blake Paterson, Baltimore, MD (US); Peter Ward, Baltimore, MD (US); Alessio Fasano, Baltimore, MD (US)

(73) Assignees: ALBA THERAPEUTICS CORPORATION, Baltimore, MD (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 118 days.

(21) Appl. No.: 15/235,313

(22) Filed: Aug. 12, 2016

(65) Prior Publication Data

US 2016/0355551 A1 Dec. 8, 2016

Related U.S. Application Data

(63) Continuation of application No. 14/971,675, filed on Dec. 16, 2015, now abandoned, which is a continuation of application No. 13/852,569, filed on Mar. 28, 2013, now abandoned, which is a continuation of application No. 12/667,192, filed as application No. PCT/US2008/068465 on Jun. 27, 2008, now abandoned.

(60) Provisional application No. 60/947,228, filed on Jun. 29, 2007.

(51) Int. Cl.
| | | |
|---|---|---|
| A61K 38/08 | (2019.01) | |
| C07K 7/06 | (2006.01) | |
| A61K 45/06 | (2006.01) | |
| A61K 9/00 | (2006.01) | |
| A61K 38/00 | (2006.01) | |

(52) U.S. Cl.
CPC ............... *C07K 7/06* (2013.01); *A61K 9/007* (2013.01); *A61K 38/08* (2013.01); *A61K 45/06* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,864,014 A | * | 1/1999 | Fasano ............... | C07K 14/28 204/456 |
| 6,670,448 B2 | * | 12/2003 | Fasano ............... | C07K 7/06 530/328 |
| 8,785,374 B2 | * | 7/2014 | Tamiz ............... | A61K 38/08 514/1.5 |

OTHER PUBLICATIONS

Dudek, Steven M. and Garcia, Joe G. N.; "Cytoskeletal regulation of pulmonary vascular permeability." J. Appl. Physiol (2001) 91(4) p. 1487-1500.*
Rocco, Patricia R. M. et al, "Effect of corticosteroid on lung parenchyma remodeling at an early phase of acute lung injury." Am. J. Respir. Crit. Care med. (2003) 168 p. 677-684.*
The ATCC web page for cell line T84, https://www.atcc.org/products/all/CCL-248.aspx#characteristics, downloaded Apr. 11, 2018.*
The ATCC web page for cell line CPAE, https://www.atcc.org/Products/All/CCL-209.aspx, downloaded Apr. 11, 2018.*

* cited by examiner

*Primary Examiner* — Fred H Reynolds
(74) *Attorney, Agent, or Firm* — Morgan, Lewis & Bockius LLP

(57) ABSTRACT

The present application provides compositions and methods for treating acute lung injury and acute respiratory distress syndrome. The methods include administering one or more tight junction antagonists to the lung of a subject in need thereof.

15 Claims, 3 Drawing Sheets

Specification includes a Sequence Listing.

Murine Lung Injury Model - Methodology**

Immune Complex formation – IV versus IT

Dose Response – Antagonist administered intratracheally

SEQUENCE LISTING

```
<160> NUMBER OF SEQ ID NOS: 24

<210> SEQ ID NO 1
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 1

Gly Arg Val Cys Val Gln Pro Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 2

Gly Arg Val Cys Val Gln Asp Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 3

Gly Arg Val Leu Val Gln Pro Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 4

Gly Arg Val Leu Val Gln Asp Gly
1               5
```

```
<210> SEQ ID NO 5
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 5

Gly Arg Leu Cys Val Gln Pro Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 6

Gly Arg Leu Cys Val Gln Asp Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 7

Gly Arg Leu Leu Val Gln Pro Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 8

Gly Arg Leu Leu Val Gln Asp Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 9

Gly Arg Gly Cys Val Gln Pro Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 10

Gly Arg Gly Cys Val Gln Asp Gly
1               5

<210> SEQ ID NO 11
```

```
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 11

Gly Arg Gly Leu Val Gln Pro Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 12

Gly Arg Gly Leu Val Gln Asp Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 13

Gly Gly Val Cys Val Gln Pro Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 14

Gly Gly Val Cys Val Gln Asp Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 15

Gly Gly Val Leu Val Gln Pro Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 16

Gly Gly Val Leu Val Gln Asp Gly
1               5

<210> SEQ ID NO 17
<211> LENGTH: 8
```

<212> TYPE: PRT
<213> ORGANISM: Artificial Sequence
<220> FEATURE:
<223> OTHER INFORMATION: Tight junction antagonist

<400> SEQUENCE: 17

Gly Gly Leu Cys Val Gln Pro Gly
1               5

<210> SEQ ID NO 18
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 18

Gly Gly Leu Cys Val Gln Asp Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 19

Gly Gly Leu Leu Val Gln Pro Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 20

Gly Gly Leu Leu Val Gln Asp Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 21

Gly Gly Gly Cys Val Gln Pro Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 22

Gly Gly Gly Cys Val Gln Asp Gly
1               5

<210> SEQ ID NO 23
<211> LENGTH: 8
<212> TYPE: PRT

-continued

```
<213> ORGANISM: Artificial Sequence
<220> FEATURE:
<223> OTHER INFORMATION: Tight junction antagonist

<400> SEQUENCE: 23

Gly Gly Gly Leu Val Gln Pro Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 24

Gly Gly Gly Leu Val Gln Asp Gly
1               5
```

USE OF TIGHT JUNCTION ANTAGONISTS IN THE TREATMENT OF ACUTE LUNG INJURY AND ACUTE RESPIRATORY DISTRESS SYNDROME

CROSS REFERENCE TO RELATED APPLICATIONS

This application is a continuation of U.S. patent application Ser. No. 14/971,675, filed Dec. 16, 2015, which is a continuation of U.S. patent application Ser. No. 13/852,569, filed Mar. 28, 2013, which is a continuation of U.S. patent application Ser. No. 12/667,192, which is the U.S. national stage of PCT/US2008/068465, filed Jun. 27, 2008, which claims priority to and the benefit of U.S. Provisional Patent Application No. 60/947,228, filed Jun. 29, 2007, the entire contents of all of which are hereby incorporated by reference in their entireties.

BACKGROUND

Acute Respiratory Distress Syndrome (ARDS) presents in about 150,000 individuals in the US annually, with a mortality rate of 30-50%. ARDS occurs in response to diverse forms of severe injury, in which lung edema results in respiratory failure. The current standard of care for ARDS is limited to the management of the disease through supportive mechanical ventilation. The loss of endothelial barrier integrity is central to the pulmonary edema that occurs in ARDS.

Triggering causes for Acute Lung Injury (ALI) including ARDS can, for example, be diffuse pulmonary infections (e.g. due to viruses, bacteria, fungi), aspiration of liquids (e.g. gastric juice or water), inhalation of toxins or irritants (e.g. chlorine gas, nitrogen oxides, smoke), direct or indirect trauma (e.g. multiple fractures or pulmonary contusion), systemic reactions to inflammations outside the lung (e.g. hemorrhagic pancreatitis, gram-negative septicemia), transfusions of high blood volumes or alternatively after cardiopulmonary bypass.

The pulmonary vascular endothelium lines the intravascular space and presents a selective barrier that actively regulates paracellular movement of circulating fluid, macromolecules, and cells, into extravascular tissues and compartments. Loss of this endothelial barrier integrity is the central defect found in ALI and ARDS. The host response to a wide range of injurious stimuli includes the biosynthesis and release of endogenous mediators, some of which can open the paracellular pathway in lung microvascular endothelia. Several of these mediators have been identified, including tumor necrosis factor α, interleukin-1, thrombospondin-1, and SPARC/osteonectin, and these mediators have been established as factors that disrupt endothelial barrier integrity. In recent preliminary studies, we found that ΔG, the active domain of zonula occludens toxin (ZOT) of *Vibrio cholerae*, increases paracellular permeability across human lung microvascular endothelial cells (HMVEC-Ls).

ZOT and ΔG have been previously identified as tight junction agonists, i.e., compounds that mediate or facilitate or augment the physiological, transient opening of tight junctions that form a barrier between adjacent epithelial cells. The ability of ZOT and ΔG to open tight junctions has been used to facilitate the transfer of macromolecule across epithelial barriers (see U.S. Pat. No. 5,665,389 and Salama et al. *J. Pharmacology and Experimental Therapeutics* 312 (1):199-205, 2005). ZOT has been shown to act as a tight junction agonist that allows opening of tight junctions between adjacent mucosal epithelial cells. Compounds that antagonize the opening of tight junctions have been identified (see U.S. Pat. Nos. 6,458,925, 6,670,448, 6,936,689 and 7,189,696). One such antagonist is currently in Phase II clinical trials for the treatment of celiac disease where it protects against loss of gut mucosal barrier function.

There remains a need in the art for compositions and methods for the treatment of ALI and ARDS. These and other needs are met by the present invention.

SUMMARY OF THE INVENTION

The present invention provides compositions and methods for the treatment of an excessive or undesirable permeability of lung tissue containing tight junctions. Methods of the invention may include administering to a subject in need thereof a composition comprising a tight junction antagonist. In some embodiments, a subject is any mammal, for example, a human. In some embodiments, a tight junction antagonist may be a peptide, for example, a peptide comprising a sequence selected from the group consisting of SEQ ID NOs:1-24. In some embodiments, a tight junction antagonist may be a peptide, for example, a peptide comprising the sequence G-G-V-L-V-Q-P-G (SEQ ID NO:15). In some embodiments, a tight junction antagonist may consist of the sequence G-G-V-L-V-Q-P-G (SEQ ID NO:15).

In some embodiments, the present invention provides compositions and methods for the treatment of acute lung injury. Such methods may comprise administering to a subject in need thereof a composition comprising a tight junction antagonist. In some embodiments, a subject is any mammal, for example, a human. In some embodiments, a tight junction antagonist may be a peptide, for example, a peptide comprising a sequence selected from the group consisting of SEQ ID NOs:1-24. In some embodiments, a tight junction antagonist may be a peptide, for example, a peptide comprising the sequence G-G-V-L-V-Q-P-G (SEQ ID NO:15). In some embodiments, a tight junction antagonist may consist of the sequence G-G-V-L-V-Q-P-G (SEQ ID NO:15).

In some embodiments, the present invention provides materials and method for the treatment of acute respiratory distress syndrome. Such methods may include administering to a subject in need thereof a composition comprising a tight junction antagonist. In some embodiments, a subject is any mammal, for example, a human. In some embodiments, a tight junction antagonist may be a peptide, for example, a peptide comprising a sequence selected from the group consisting of SEQ ID NOs:1-24. In some embodiments, a tight junction antagonist may be a peptide, for example, a peptide comprising the sequence G-G-V-L-V-Q-P-G (SEQ ID NO:15). In some embodiments, a tight junction antagonist may consist of the sequence G-G-V-L-V-Q-P-G (SEQ ID NO:15). Compositions for use in the methods of the invention may also comprise one or more additional components. Examples of additional components include, but are not limited to, aminosalicylates, corticosteroids, immunomodulators, antibiotics, cytokines, chemokines and biologic therapeutics. Compositions for use in the methods of the invention may be formulated in any manner known to those skilled in the art, for example, the compositions may be formulated for pulmonary delivery.

DETAILED DESCRIPTION OF THE INVENTION

Antagonists of Tight Junction Opening

Figure 1:
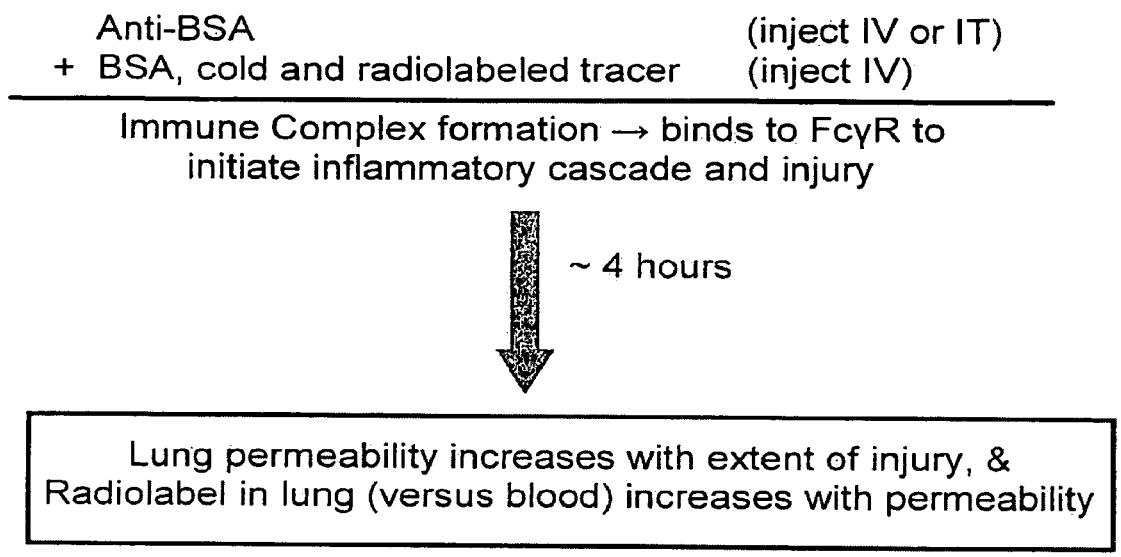
FIG. 1 is a schematic representation of the experimental protocol used in the examples.

As used herein, tight junction antagonists prevent, inhibit or reduce the opening of tight junctions, for example, the opening of tight junctions induced by a tight junction agonist. A tight junction antagonist may bind to the receptor that mediates tight junction agonist induced opening of tight junctions. For example, a tight junction antagonist may bind to the ZOT receptor and prevent, inhibit, reduce or reverse the tight junction opening triggered by the tight junction agonist ZOT.

As used herein a subject is any animal, e.g., mammal, upon which methods of the invention may be practiced and/or to which materials of the present invention may be administered. Subjects include, but are not limited to, humans.

Any antagonist of tight junction opening may be used in the practice of the present invention. For example, antagonists of the invention may comprise peptide antagonists. Examples of peptide antagonists include, but are not limited to, peptides that comprise an amino acid sequence selected from the group consisting of

```
                                   (SEQ ID NO: 1)
Gly Arg Val Cys Val Gln Pro Gly, (SEQ ID NO: 2)
Gly Arg Val Cys Val Gln Asp Gly, (SEQ ID NO: 3)
Gly Arg Val Leu Val Gln Pro Gly, (SEQ ID NO: 4)
Gly Arg Val Leu Val Gln Asp Gly, (SEQ ID NO: 5)
Gly Arg Leu Cys Val Gln Pro Gly, (SEQ ID NO: 6)
Gly Arg Leu Cys Val Gln Asp Gly, (SEQ ID NO: 7)
Gly Arg Leu Leu Val Gln Pro Gly, (SEQ ID NO: 8)
Gly Arg Leu Leu Val Gln Asp Gly, (SEQ ID NO: 9)
Gly Arg Gly Cys Val Gln Pro Gly, (SEQ ID NO: 10)
Gly Arg Gly Cys Val Gln Asp Gly, (SEQ ID NO: 11)
Gly Arg Gly Leu Val Gln Pro Gly, (SEQ ID NO: 12)
Gly Arg Gly Leu Val Gln Asp Gly, (SEQ ID NO: 13)
Gly Gly Val Cys Val Gln Pro Gly, (SEQ ID NO: 14)
Gly Gly Val Cys Val Gln Asp Gly,
```

-continued

```
                                  (SEQ ID NO: 15)
Gly Gly Val Leu Val Gln Pro Gly, (SEQ ID NO: 16)
Gly Gly Val Leu Val Gln Asp Gly, (SEQ ID NO: 17)
Gly Gly Leu Cys Val Gln Pro Gly, (SEQ ID NO: 18)
Gly Gly Leu Cys Val Gln Asp Gly, (SEQ ID NO: 19)
Gly Gly Leu Leu Val Gln Pro Gly, (SEQ ID NO: 20)
Gly Gly Leu Leu Val Gln Asp Gly, (SEQ ID NO: 21)
Gly Gly Gly Cys Val Gln Pro Gly, (SEQ ID NO: 22)
Gly Gly Gly Cys Val Gln Asp Gly, (SEQ ID NO: 23)
Gly Gly Gly Leu Val Gln Pro Gly,
and (SEQ ID NO: 24)
Gly Gly Gly Leu Val Gln Asp Gly
```

Examples of peptide antagonists include, but are not limited to, peptides that consist of an amino acid sequence selected from the group consisting of SEQ ID NOs:1-24. Examples of peptide antagonists of tight junctions can be found in U.S. Pat. Nos. 6,458,925, 6,670,448, 6,936,689, and 7,189,696 the entire contents of which are specifically incorporate herein by reference.

When the antagonist is a peptide, any length of peptide may be used. Generally, the size of the peptide antagonist will range from about 6 to about 100, from about 6 to about 90, from about 6 to about 80, from about 6 to about 70, from about 6 to about 60, from about 6 to about 50, from about 6 to about 40, from about 6 to about 30, from about 6 to about 25, from about 6 to about 20, from about 6 to about 15, from about 6 to about 14, from about 6 to about 13, from about 6 to about 12, from about 6 to about 11, from about 6 to about 10, from about 6 to about 9, or from about 6 to about 8 amino acids in length. Peptide antagonists of the invention may be from about 8 to about 100, from about 8 to about 90, from about 8 to about 80, from about 8 to about 70, from about 8 to about 60, from about 8 to about 50, from about 8 to about 40, from about 8 to about 30, from about 8 to about 25, from about 8 to about 20, from about 8 to about 15, from about 8 to about 14, from about 8 to about 13, from about 8 to about 12, from about 8 to about 11, or from about 8 to about 10 amino acids in length. Peptide antagonists of the invention may be from about 10 to about 100, from about 10 to about 90, from about 10 to about 80, from about 10 to about 70, from about 10 to about 60, from about 10 to about 50, from about 10 to about 40, from about 10 to about 30, from about 10 to about 25, from about 10 to about 20, from about 10 to about 15, from about 10 to about 14, from about 10 to about 13, or from about 10 to about 12 amino acids in length. Peptide antagonists of the invention may be from about 12 to about 100, from about 12 to about 90, from about 12 to about 80, from about 12 to about 70, from about 12 to about 60, from about 12 to about 50, from about 12 to about 40, from about 12 to about 30, from about 12 to about 25, from about 12 to about 20, from about 12 to about 15, or from about 12 to about 14 amino acids in length.

Peptide antagonists of the invention may be from about 15 to about 100, from about 15 to about 90, from about 15 to about 80, from about 15 to about 70, from about 15 to about 60, from about 15 to about 50, from about 15 to about 40, from about 15 to about 30, from about 15 to about 25, from about 15 to about 20, from about 19 to about 15, from about 15 to about 18, or from about 17 to about 15 amino acids in length.

The peptide antagonists can be chemically synthesized and purified using well-known techniques, such as described in *High Performance Liquid Chromatography of Peptides and Proteins: Separation Analysis and Conformation*, Eds. Mant et al., C.R.C. Press (1991), and a peptide synthesizer, such as Symphony (Protein Technologies, Inc); or by using recombinant DNA techniques, i.e., where the nucleotide sequence encoding the peptide is inserted in an appropriate expression vector, e.g., an *E. coli* or yeast expression vector, expressed in the respective host cell, and purified therefrom using well-known techniques.

Compositions

Typically, compositions, such as pharmaceutical compositions, comprising a tight junction antagonist (e.g., peptide tight junction antagonist) comprise a pharmaceutically effective amount of the antagonist. The pharmaceutically effective amount of antagonist (e.g., peptide tight junction antagonist) employed in any given composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation.

Generally, the amount of antagonist used for preventing, ameliorating and/or treating a disease in a subject will be in the range of about 1.0 µg to 1 g, preferably about 1 mg to about 1000 mg, or from about 10 mg to about 100 mg, or from about 10 mg to about 50 mg, or from about 10 mg to about 25 mg of antagonist per dose.

Compositions of the invention may comprise one or more tight junction antagonists at a level of from about 0.1 wt % to about 20 wt %, from about 0.1 wt % to about 18 wt %, from about 0.1 wt % to about 16 wt %, from about 0.1 wt % to about 14 wt %, from about 0.1 wt % to about 12 wt %, from about 0.1 wt % to about 10 wt %, from about 0.1 wt % to about 8 wt %, from about 0.1 wt % to about 6 wt %, from about 0.1 wt % to about 4 wt %, from about 0.1 wt % to about 2 wt %, from about 0.1 wt % to about 1 wt %, from about 0.1 wt % to about 0.9 wt %, from about 0.1 wt % to about 0.8 wt %, from about 0.1 wt % to about 0.7 wt %, from about 0.1 wt % to about 0.6 wt %, from about 0.1 wt % to about 0.5 wt %, from about 0.1 wt % to about 0.4 wt %, from about 0.1 wt % to about 0.3 wt %, or from about 0.1 wt % to about 0.2 wt % of the total weight of the composition. Compositions of the invention may comprise one or more tight junction antagonists at a level of about 0.1 wt %, about 0.2 wt %, about 0.3 wt %, about 0.4 wt %, about 0.5 wt %, about 0.6 wt %, about 0.7 wt %, about 0.8 wt %, or about 0.9 wt % based on the total weight of the composition.

Compositions of the invention may comprise one or more tight junction antagonists at a level of from about 1 wt % to about 20 wt %, from about 1 wt % to about 18 wt %, from about 1 wt % to about 16 wt %, from about 1 wt % to about 14 wt %, from about 1 wt % to about 12 wt %, from about 1 wt % to about 10 wt %, from about 1 wt % to about 9 wt %, from about 1 wt % to about 8 wt %, from about 1 wt % to about 7 wt %, from about 1 wt % to about 6 wt %, from about 1 wt % to about 5 wt %, from about 1 wt % to about 4 wt %, from about 1 wt % to about 3 wt %, or from about 1 wt % to about 2 wt % of the total weight of the composition. Compositions of the invention may comprise one or more tight junction effectors at a level of about 1 wt %, about 2 wt %, about 3 wt %, about 4 wt %, about 5 wt %, about 6 wt %, about 7 wt %, about 8 wt %, or about 9 wt % based on the total weight of the composition.

Compositions of the invention may be formulated for pulmonary delivery (e.g., may be pulmonary dosage forms). Typically such compositions may be provided as pharmaceutical aerosols, e.g., solution aerosols or powder aerosols. Those of skill in the art are aware of many different methods and devices for the formation of pharmaceutical aerosols, for example, those disclosed by Sciarra and Sciarra, *Aerosols*, in *Remington: The Science and Practice of Pharmacy*, 20th Ed., Chapter 50, Gennaro et al. Eds., Lippincott, Williams and Wilkins Publishing Co., (2000).

In one embodiment, the dosage forms are in the form of a powder aerosol (i.e, comprise particles). These are particularly suitable for use in inhalation delivery systems. Powders may comprise particles of any size suitable for administration to the lung.

Powder formulations may optionally contain at least one particulate pharmaceutically acceptable carrier known to those of skill in the art. Examples of suitable pharmaceutical carriers include, but are not limited to, saccharides, including monosaccharides, disaccharides, polysaccharides and sugar alcohols such as arabinose, glucose, fructose, ribose, mannose, sucrose, trehalose, lactose, maltose, starches, dextran, mannitol or sorbitol. In one embodiment, a powder formulation may comprise lactose as a carrier.

Powder formulations may be contained in any container known to those in the art. Containers may be capsules of, for example, gelatin or plastic, or in blisters (e.g. of aluminum or plastic), for use in a dry powder inhalation device. In some embodiments, the total weight of the formulation in the container may be from about 5 mg to about 50 mg. In other embodiments, powder formulations may be contained in a reservoir in a multi-dose dry powder inhalation device adapted to deliver a suitable amount per actuation.

Powder formulations typically comprise small particles. Suitable particles can be prepared using any means known in the art, for example, by grinding in an airjet mill, ball mill or vibrator mill, sieving, microprecipitation, spray-drying, lyophilisation or controlled crystallisation. Typically, particles will be about 10 microns or less in diameter. Particles for use in the compositions of the invention may have a diameter of from about 0.1 microns to about 10 microns, from about 0.1 microns to about 9 microns, from about 0.1 microns to about 8 microns, from about 0.1 microns to about 7 microns, from about 0.1 microns to about 6 microns, from about 0.1 microns to about 5 microns, from about 0.1 microns to about 4 microns, from about 0.1 microns to about 3 microns, from about 0.1 microns to about 2 microns, from about 0.1 microns to about 1 micron, from about 0.1 microns to about 0.5 microns, from about 1 micron to about 10 microns, from about 1 micron to about 9 microns, from about 1 micron to about 8 microns, from about 1 micron to about 7 microns, from about 0.1 micron to about 6 microns, from about 1 micron to about 5 microns, from about 1 micron to about 4 microns, from about 1 micron to about 3 microns, from about 1 micron to about 2 microns, from about 2 microns to about 10 microns, from about 2 microns to about 9 microns, from about 2 microns to about 8 microns, from about 2 microns to about 7 microns, from about 2 microns to about 6 microns, from about 2 microns to about 5 microns, from about 2 microns to about 4 microns, or from about 2 microns to about 3 microns. In some embodiments, particles for use in the invention may be about 1 micron, about 2 microns, about 3 microns, about 4 microns, about 5 microns, about 6 microns, about 7 microns, about 8 microns, about 9 microns, or about 10 microns in diameter.

In one embodiment, the dosage forms are in the form of a solution aerosol (i.e., comprise droplets). Typically, droplets will be about 10 microns or less in diameter. Droplets for use in the compositions of the invention may have a diameter of from about 0.1 microns to about 10 microns, from about 0.1 microns to about 9 microns, from about 0.1 microns to about 8 microns, from about 0.1 microns to about 7 microns, from about 0.1 microns to about 6 microns, from about 0.1 microns to about 5 microns, from about 0.1 microns to about 4 microns, from about 0.1 microns to about 3 microns, from about 0.1 microns to about 2 microns, from about 0.1 microns to about 1 micron, from about 0.1 microns to about 0.5 microns, from about 1 micron to about 10 microns, from about 1 micron to about 9 microns, from about 1 micron to about 8 microns, from about 1 micron to about 7 microns, from about 1 micron to about 6 microns, from about 1 micron to about 5 microns, from about 1 micron to about 4 microns, from about 1 micron to about 3 microns, from about 1 micron to about 2 microns, from about 2 microns to about 10 microns, from about 2 microns to about 9 microns, from about 2 microns to about 8 microns, from about 2 microns to about 7 microns, from about 2 microns to about 6 microns, from about 2 microns to about 5 microns, from about 2 microns to about 4 microns, or from about 2 microns to about 3 microns. In some embodiments, particles and/or droplets for use in the invention may be about 1 micron, about 2 microns, about 3 microns, about 4 microns, about 5 microns, about 6 microns, about 7 microns, about 8 microns, about 9 microns, or about 10 microns in diameter.

In addition to a tight junction antagonist, compositions of the invention may further comprise one or more additional therapeutic agents, particularly therapeutic agents conventionally used for treating lung conditions such as ALI and ARDS. Such additional therapeutic agents include, but are not limited to, steroids and other anti-inflammatory compounds. Suitable therapeutic agents may include one or more of aminosalicylates, corticosteroids, immunomodulators, antibiotics, cytokines, chemokines and biologic therapies.

Compositions of the invention may also comprise one or more pharmaceutically acceptable excipients. Suitable excipients include, but are not limited to, buffers, buffer salts, bulking agents, salts, surface active agents, acids, bases, sugars, and binders.

Methods of Use

The compositions of the invention can be used for preventing, slowing the onset of, ameliorating and/or treating ALI and ARDS. Typically, compositions may be administered one or more times each day in an amount suitable to prevent, reduce the likelihood of an attack of, or reduce the severity of an attack of the underlying disease condition.

In some embodiments, compositions of the invention may be given repeatedly over a protracted period, i.e., may be chronically administered. Typically, compositions may be administered one or more times each day in an amount suitable to treat ALI and ARDS.

In some embodiments, compositions of the invention may be used to treat acute symptoms of ALI and ARDS. Typically, embodiments of this type will require administration of the compositions of the invention to a subject undergoing an acute episode in an amount suitable to reduce the severity of the symptoms. One or more administration may be used.

A composition according to the present invention may be pre-mixed prior to administration, or can be formed in vivo when two or more components (e.g., a tight junction antagonist and an additional therapeutic agent) are administered within 24 hours of each other. When administered separately, the components may be administered in either order (e.g. tight junction antagonist first followed by additional therapeutic agent or additional therapeutic agent first followed by tight junction antagonist). The components can be administered within a time span of about 12 hours, about 8 hours, about 4 hours, about 2 hours, about 1 hour, about 0.5 hour, about 0.25 hour, about 0.1 hour, about 1 minute, about 0.5 minute, or about 0.1 minute.

Administration of the compositions described above, e.g., compositions comprising one or more tight junction antagonists and optionally comprising one or more additional therapeutic agents, may be by inhalation. For example, one or more tight junction antagonists and one or more additional therapeutic agents or a mixture thereof, may be in inhalable form. An example of an inhalable form is an atomizable composition such as an aerosol comprising the tight junction antagonist, either alone or in combination with one or more additional therapeutic agents, in solution or dispersion in a propellant, or a nebulizable composition comprising a solution or dispersion of the active ingredient in an aqueous, organic or aqueous/organic medium. For example, the inhalable form of the compositions of the invention may be an aerosol comprising a mixture of one or more tight junction antagonists and one or more additional therapeutic agents in solution or dispersion in a propellant, or a combination of an aerosol containing one or more tight junction antagonists in solution or dispersion in a propellant with an aerosol containing one or more therapeutic agents in solution or dispersion in a propellant. In another example, the inhalable form of the compositions of the invention my be a nebulizable composition comprising a dispersion of one or more tight junction antagonists and one or more additional therapeutic agents in an aqueous, organic or aqueous/organic medium, or a combination of a dispersion of one or more tight junction antagonists with a dispersion of one or more additional therapeutic agents in such a medium.

Compositions of the invention may be administered in conjunction with one or more additional therapeutic agents, particularly therapeutic agents used conventionally for treating lung conditions such as ALI and ARDS. Such additional therapeutic agents include, but are not limited to, steroids and other anti-inflammatory compounds. Suitable therapeutic agents may include one or more of aminosalicylates, corticosteroids, immunomodulators, antibiotics, cytokines, chemokines and biologic therapies.

Compositions of the invention and one or more additional therapeutic agents may be administered simultaneously, or alternatively compositions of the invention and one or more additional therapeutic agents may not be administered simultaneously. Furthermore, compositions of the invention may be administered prior to administration of one or more additional therapeutic agents, or alternatively compositions of the invention may be administered subsequent to administration of one or more additional therapeutic agents.

The following examples are provided for illustrative purposes only, and are in no way intended to limit the scope of the present invention.

EXAMPLES

The IgG immune complex model is a well established model of lung injury and is shown schematically in FIG. 1.

Briefly, a heterologous antibody mix containing antibodies to a known antigen are injected into an animal intravenously (IV) or intratracheally (IT). The known antigen and a small amount of radiolabelled known antigen are injected into the animal IV. This results in immune complex (IC) formation between the antigen and the cognate antibodies in the heterologous antibody mix. The immune complex binds to binds to the Fe gamma receptor (FcγR) and this initiates an inflammatory cascade and leads to injury. One of the results of the inflammatory cascade is an increase in lung permeability that increases with extent of injury. The increase in lung permeability is quantified by measuring the radiolabelled antigen present in lung versus blood where radiolabel in the lung versus blood increases with permeability. (See Johnson and Ward, *J. Clin. Investigation* 54:349-357, 1974).

Figure 2:
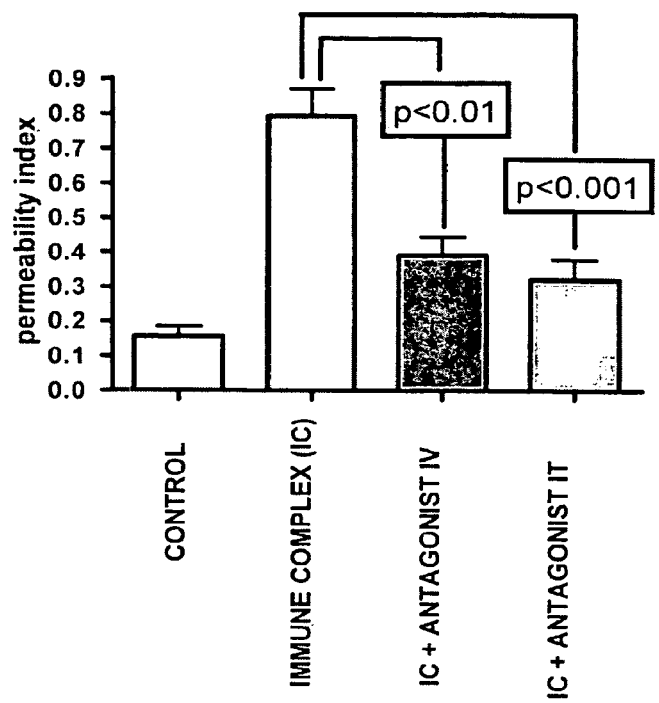
FIG. 2 is a bar graph showing lung permeability as a function of the treatment regimen comparing IV versus IT administration of tight junction antagonist.

FIG. 2 shows the results of an experiment where 4-5 mice per arm were treated as described above where the known antigen was bovine serum albumin (BSA) the heterologous antibody mix included antibody to bovine serum albumin (anti-BSA) and the treatment was carried out in the presence and absence of tight junction antagonist SEQ ID NO:15.

FIG. 2 shows a comparison of the change in lung permeability resulting from IC formation in response to the treatment described above in the presence and absence of tight junction antagonist as well as a comparison of the effects of IV versus IT administration of tight junction antagonist.

Figure 3:
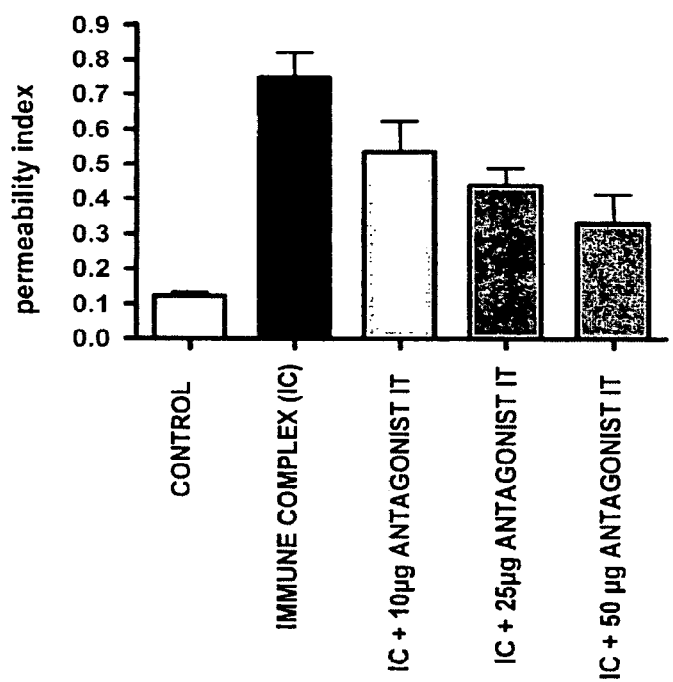
FIG. 3 is a bar graph showing lung permeability as a function of the amount of tight junction antagonist applied with anti-BSA antibody intratracheally.

FIG. 3 shows the results of varying the dose of SEQ ID NO:15 administered with the anti-BSA antibodies delivered IT.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for treating acute respiratory distress syndrome or acute lung injury comprising:

administering to a human subject in need thereof, a composition comprising a peptide tight junction antagonist, wherein the tight junction antagonist is a peptide having the amino acid sequence GGVLVQPG (SEQ ID NO: 15).

2. The method according to claim 1, wherein the peptide consists of GGVLVQPG (SEQ ID NO: 15).

3. The method according to claim 1, wherein the composition is administered in conjunction with an additional therapeutic agent.

4. The method according to claim 3, wherein the composition and the additional therapeutic agent are administered simultaneously.

5. The method according to claim 3, wherein the composition and the additional therapeutic agent are not administered simultaneously.

6. The method according to claim 3, wherein the composition further comprises the additional therapeutic agent.

7. The method according to claim 3, wherein the additional therapeutic agent is selected from the group consisting of aminosalicylates, corticosteroids, immunomodulators, antibiotics, cytokines, chemokines, and biologic therapeutics.

8. The method according to claim 1, wherein the composition is formulated for pulmonary delivery.

9. The method of claim 1, wherein the subject has acute respiratory distress syndrome.

10. The method of claim 1, wherein the subject has acute lung injury.

11. The method of claim 1, wherein the composition is a pharmaceutical aerosol.

12. The method of claim 1, wherein the composition is a solution aerosol.

13. The method of claim 1, wherein the composition is a powder aerosol.

14. The method of claim 6, wherein the additional therapeutic agent is an aminosalicylate or corticosteroid.

15. The method of claim 1, wherein the composition is administered intravenously (IV) or intratracheally (IT).

* * * * *